United States Patent [19]

Cresap, III

[11] Patent Number: 4,934,320

[45] Date of Patent: Jun. 19, 1990

[54] ANIMAL RESTRAINING DEVICE

[76] Inventor: Logan Cresap, III, 22 Jaipur La., Saratoga, N.Y. 12866

[21] Appl. No.: 271,996

[22] Filed: Nov. 16, 1988

[51] Int. Cl.$^5$ .......................... A61D 3/00; A61B 6/04
[52] U.S. Cl. .................................... 119/103; 128/872; 370/209
[58] Field of Search .................... 119/103, 96, 143; 378/208, 209; 128/872

[56] References Cited

U.S. PATENT DOCUMENTS

| | | | |
|---|---|---|---|
| 2,027,318 | 1/1936 | Nelson | 378/209 |
| 2,284,448 | 5/1942 | Reinholz | 128/872 |
| 2,682,672 | 7/1954 | Moore | 128/872 |
| 2,705,475 | 4/1955 | Johnisee | 119/103 |
| 3,181,180 | 5/1965 | Moore | 128/872 |
| 3,286,693 | 11/1966 | Clark, Jr. | 119/103 |
| 3,732,944 | 5/1973 | Kendall | 180/103 |
| 4,657,003 | 4/1987 | Wirtz | 128/133 |

FOREIGN PATENT DOCUMENTS 11858 3/1933 Australia .............................. 119/103

Primary Examiner—John Weiss
Attorney, Agent, or Firm—Schmeiser, Morelle & Watts

[57] ABSTRACT

A device for restraining an animal to an x-ray table while conducting veterinary radiography. The animal restraining device comprises an impermeable, pliant sheet for covering the body of an animal. The pliant sheet is encased by a tubular frame which is attached by hinges to a rigid, planer surface for placement on an x-ray table or to the x-ray table itself. With the animal positioned on the rigid surface or table, the frame and sheet combination is placed in registry with the table as the head or the animal is brought through a head-receiving orifice in the sheet. The tubular frame is connected to an external vacuum source. With the source activated, air is drawn from the apparatus through apertures in the tubular frame, thereby creating a partial vacuum within the chamber defined by the sheet and the table. The pliant sheet closely conforms to the body of the animal, thus immobilizing it by the application of an evenly distributed, but variable, pressure.

8 Claims, 2 Drawing Sheets

ANIMAL RESTRAINING DEVICE

FIELD OF THE INVENTION

The present invention relates generally to restraining devices. More particularly, this invention is an animal restraining device for use while conducting veterinary radiography.

BACKGROUND OF THE INVENTION

Animal restraints as heretofore known generally and simply comprise straps for securing an animal to an examination table or the like. Disadvantageously, these devices are often difficult to use. In particular, a seemingly unnecessary and unfortunate amount of force and dexterity are needed to position the animal on the table in order to secure it thereto. Often, two or more persons must cooperate in order to effectively and appropriately position and restrain the animal.

Animal and personal safety are major concerns when it becomes necessary to restrain an animal. Instinctively, animals fight restraining forces by biting, scratching, and attempting escape. This is especially the case for injured animals in need of medical care. Such violent opposition by the animal many times results in injury to the veterinarian or the x-ray technician or any other person involved. Additionally and unfortunately, an injured animal in need of treatment which struggles violently often experiences further injuries, thus exacerbating the situation.

Another problem with the utilization of straps as restraining devices is that the straps themselves are often the causes of injury to the animal. For instance, a tightly secured strap may cause cuts and bruises to a struggling animal. And, if the strap is directly applied to an injured area, the injury is likely to be aggravated.

Still another problem with the conventional animal restraining devices is the exposure of the veterinarian or x-ray technician to x-rays. Such exposure often occurs as a result of having to manually hold the animal during the conduct of x-rays when the straps prove inadequate.

The present inventor has overcome the above-described problems with the animal restraining devices of the prior art by developing a device which is easy and safe to use, thereby reducing the trauma of a veterinary examination to an animal. The animal restraint of the present invention enables the application of an evenly distributed pressure over the body of the animal which is sufficient for immobilization purposes, yet which is gentle enough to avoid further injury to the animal being treated.

The major advantages of the invention are set forth in part herein and in part will be obvious herefrom, or may be learned by practice with the invention, the same being realized and attained by means of the instrumentalities and combinations pointed out in the appended claims.

SUMMARY OF THE INVENTION

The present invention is a device for restraining an animal to an x-ray table while conducting veterinary radiography. The device comprises an impermeable, pliant sheet for covering the body of an animal and a tubular frame encasing the sheet which has sealing means associated therewith for airtightly securing the periphery of the sheet to a rigid surface, hereinafter referred to as an examination table, for placement on an x-ray table or, in an alternate embodiment, to the x-ray table itself. Because the sheet is pliant it conforms evenly and smoothly over the radiographic image area and gently immobilzes the animal. The apparatus is so designed as to present a constant cross sectional density in the image area to avoid distorting the final radiographic image, but still evenly evacuate the chamber to achieve sufficient immobilization. This is accomplished by having a sheet area so in excess of the area covered by the sheet that while the sheet stretches smoothly over the animal it forms folds which define conduits in the nonimage areas and these conduits serve as passageways for the air being evacuated from under the sheet. I have found that a five percent excess in sheet area will achieve the above described effect. The tubular frame is attached by hinges to one side of the table so that the sheet and table form a chamber for enveloping an animal when the frame is placed in registry with the table. An opening is further provided in the sheet for maintaining the animal's head exteriorly of the vacuum chamber, and a collar is applied to the neck of the animal in order to effect an airtight seal at the location of the head opening. An external vacuum source is applied to the vacuum chamber through apertures in the tubular frame, thereby causing the pliant sheet to conform to the body of the animal. The animal is thus immobilized by the application of an evenly distributed, but variable, pressure over its body. Substantially complete motionlessness or immobilization is essential since the exposure duration for a typical veterinary radiograph is 1/100th of a second and any movement will result in an indistinct radiograph.

The accompanying drawings, referred to herein and constituting a part hereof, illustrate preferred embodiments of the invention, and together with the description, serve to explain the principles of the invention.

BRIEF DESCRIPTION OF THE DRAWINGS

Of the drawings:

FIG. 3 is a cross-sectional view from the left side of the present invention with the animal restraining device in a closed and unused position;

FIG. 4 is a partial perspective view illustrating how the collar engages the pliant sheet.

DETAILED DESCRIPTION OF THE DRAWINGS

Figure 1:
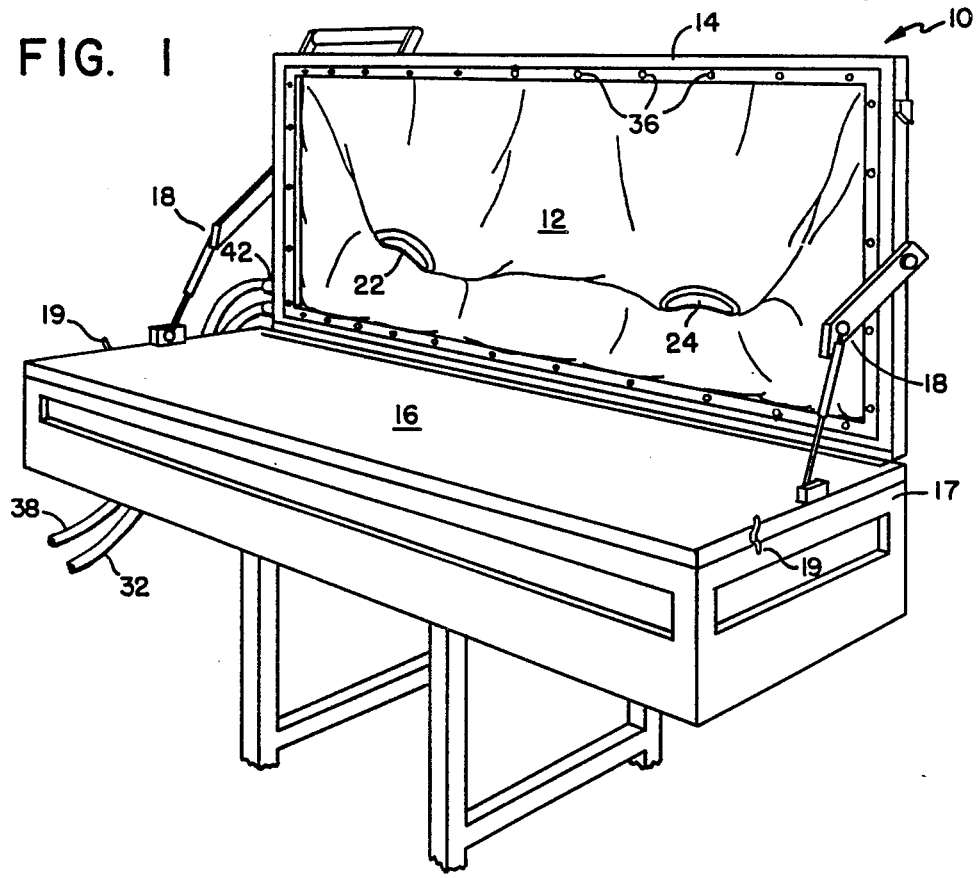
FIG. 1 is a perspective view of the animal restraining device of the present invention.
Figure 2:
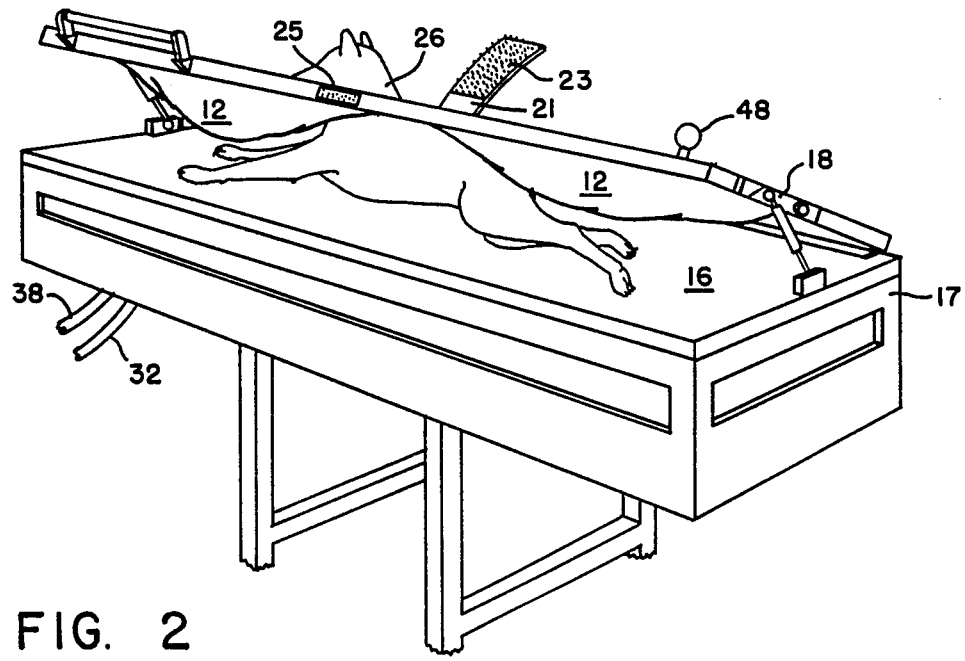
FIG. 2 is a perspective view of the animal restraining device in use.

With reference to FIGS. 1 through 3, the animal restraining device of the present invention is shown, generally designated by the numeral 10.

The animal restraining device 10 comprises an impermeable, pliant sheet 12, preferably made of a layer of rubber. The layer of rubber is thin so that only slight attenuation of the x-rays occurs during use of the device 10. The sheet 12 is ⅛ of an inch thick and bounded peripherally by a rectangular, tubular frame 14. The ares of the sheet 12 is so in excess of the boundary of the tubular frame 14 to allow the formulation of conduits for the evacuation of air. In the preferred embodiment of the present invention, one side of the rectangular frame 14 is connected by a hinge (not shown) to a rigid, planar surface or examination table 16 for placement on an x-ray table 17. In an alternate embodiment, the frame 14 is directly attached to the x-ray table 17. The frame 14 and sheet 12 combination is manually adjustable from the upright position, as shown in FIG. 1, to a horiZontal position, as shown in FIG. 3, whereby the frame 14 is in registry with the table 16. The sheet 12 and the table 16 thus define a chamber for receiving an animal, as illustrated in FIG. 2. Additionally, a counterbalance mechanism 18, which is mounted between the examination table 16 and the frame 14, maintains the frame 14 in an open position, which is variable between thirty and ninety degrees with respect to the table 16; the chamber will, thus, remain open during the positioning of the animal within the chamber or during the removal therefrom. As shown in FIG. 1, at either end of the x-ray table 17 is a cleat 19 which may be used to secure a leash attached to the animal for further head restraint. Use of a leash is further beneficial for guiding the animals head into position during positioning. In addition to the force of sheet 12 the animals head or neck may be secured by a strap 21 (shown in FIG. 2) and is secured at one end to the rear side of the tubular frame 14 and at the other end has VELCRO fastening hooks 23 which mates and are secured to a VELCRO pad 25 on the front side of tubular frame 14.

Two head-receiving orifices 22, 24 are formed in the pliant sheet 12 to maintain the animal's head externally of the vacuum chamber during use. The head-receiving orifices 22, 24 are positioned at opposite ends of the pliant sheet 12 so that the position of the animal 26 is variable relative to the table 12, depending upon the part of the animal's body to be x-rayed.

The tubular frame 14 is attachable to an external vacuum source for creating a partial vacuum within the chamber defined by the sheet 12 and the table 16. A gasket 30 on the underside of the tubular 14 frame is provided for effecting an airtight seal between the table 12 and the frame 16. A plastic 32 hose connects the external vacuum source to the tubular frame 14 through an opening 34 in the frame 14. Upon activation of the vacuum source, apertures 36 in the tubular frame 14 permit the evacuation of air from the chamber, thereby creating a partial vacuum within the chamber and causing the sheet 12 to conform closely to the body of the animal 26.

For adjusting the vacuum force within the chamber, a bleed hose 38 for permitting the flow of ambient air into the chamber is removably attached to the tubular frame 14 through another opening 40. A manually operated valve 42 enables the user to vary the size of the opening 40 in order to selectively increase and decrease the vacuum force within the chamber, as needed. To monitor the strength of the vacuum within the chamber, a vacuum gauge 44 is mounted to the tubular frame 14.

Still further, the tubular frame 14 includes a relief valve 46, which enables a quick release of the vacuum force applied to the animal 26. The quick release is accomplished by the rapid introduction of air upon removal of the valve control plug 48.

To use the animal restraining device 10 of the present invention, the animal is first positioned on the examination table 16 as the frame 14 is held upwardly by the counterbalance mechanism 18 at an angle which is variable between thirty and ninety degrees with respect to the table 16. The tubular frame 14 is then drawn downwardly toward the table. When the pliant sheet 12 meets the animal's head, the head is drawn through one of the head-receiving orifices, 22 or 24, depending upon the portion of the animal's body to be x-rayed. Then, with the gasket 30 in engagement with the surface of the table 16, a collar 50 of the same composition as the sheet 12 but only 1/32 of an inch thick for increased pliability and concommitant sealing is drawn over the head of the animal 26. Fasteners comprising hooks 52 and loops 54 well-known under the trademark VELCRO, are used to secure the collar 50 to the sheet 12. The unused head-receiving orifice is sealed by securing a smaller, thin rubber sheet (not shown) to the sheet 12 using VELCRO fasteners. Then, with the animal positioned and enclosed within the vacuum chamber, the external vacuum source is activated, thereby creating a partial vacuum within the chamber and immobilizing the animal. The partial vacuum also serves to seal the perimeter of the collar 50 to the main sheet 12.

For those animals which are so small that the x-ray film must be placed directly beneath the animal in order to obtain a clear x-ray image, the same apparatus as hereinbefore described, with modifications, may be used. First, a lead-lined stainless steel backscatter shield is placed on the table 16 of the device 10. Next, the x-ray film and screens for intensifying the image are encased in a protective covering, such as a light plastic container, and placed on the shield. Another protective covering in the form of a thin, flexible, x-ray transparent sheet is placed upon the film package. The thin protective sheet is then secured to the table by inserting pins through pinholes formed in the sheet and corresponding holes in the table. With the animal in place on the protective sheet, the device 10 is used as above described.

The invention in its broader aspects is not limited to the specific embodiments herein shown and described but departures may be made therefrom within the scope of the accompanying claims, without departing from the principles of the invention and without sacrificing its chief advantages.

What is claimed is:

1. An apparatus for restraining an animal, which comprises:
 a frame;
 a sheet of impermeable, pliant material secured within the frame, said frame being about the periphery of said sheet and secured airtightly thereto, said apparatus having an opening for the head of the animal;
 sealing means associated with said frame for securing the frame and the peripheral portion of said sheet airtightly to a support surface; and
 evacuation means secured to said sheet and attachable to an external vacuum source to withdraw air from the space around an animal on said surface under said sheet thereby creating a vacuum for restraining said animal.

2. The invention of claim 1 wherein the area of the sheet is greater than the area within the boundary of said frame.

3. An apparatus for restraining an animal which comprises:
 a sheet of impermeable, pliant material to cover the legs and body of an animal on an examination table, said sheet having an opening for the head of the animal;
 sealing means associated with said sheet for securing the peripheral portion of said sheet airtightly to an examination table;
 evacuation means including a tubular body secured to said sheet and attachable to an external vacuum source to withdraw air from the space around an animal on an examination table under said sheet; and a collar of resilient material attached to said sheet to close the opening in said sheet airtightly around the neck of the animal.

4. An apparatus for restraining an animal while conducting veterinary radiography, which comprises a rigid, planar, substantially rectangular table for supporting the body of an animal and an impermeable, pliant sheet for covering the body of the animal, said sheet further being bounded and encased by a substantially rectangular frame hingedly connected to said table along one side thereof so that said frame is moveable relative to said table to enable the positioning of the animal on said table and further within a chamber defined by said sheet and said table when said frame is placed in registry therewith, said sheet having a head-receiving orifice for maintaining the head of the animal exteriorly of the chamber, said frame having gasket means for effecting an airtight seal between said frame and said table, said frame further being of tubular construction and having apertures formed at selective intervals thereon for the evacuation of air from the chamber when an external vacuum source is applied through an opening in said tubular frame, whereby a partial vacuum develops in the chamber causing said covering to closely conform to the body of the animal while exerting an essentially constant pressure thereon, thereby restraining the animal.

5. The animal restraining apparatus of claim 4 wherein said tubular frame further comprises valve means mounted thereon for adjusting the vacuum force within the chamber, thereby enabling the application of a variable amount of pressure to the body of the animal.

6. The animal restraining apparatus of claim 4, which further comprises collar means for effecting a substantially airtight seal between the head-receiving orifice and the neck of the animal.

7. The animal restraining apparatus of claim 4, which comprises at least two head-receiving orifices at selective locations on said sheet whereby the position of the animal is variable relative to said table without requiring the reorientation of the animal restraining apparatus.

8. An apparatus for restraining an animal while conducting veterinary radiography for attachment to an x-ray table, which comprises a pliant, resilient sheet for covering the body of the animal, said sheet being bounded and encased by a substantially rectangular frame having hinge means mounted on one side thereof for hingedly attaching one side of said frame to the corresponding side of the x-ray table so that said frame is moveable relative to the x-ray table to enable the positioning of the animal on the table and further within a chamber defined by said sheet and the x-ray table when said frame is placed in registry therewith, said sheet having a head-receiving orifice for maintaining the head of the animal exteriorly of the chamber, said frame having gasket means for effecting an airtight seal between said frame and the table, said frame further being of tubular construction and having apertures formed at selective intervals thereon for the evacuation of air from the chamber when a vacuum source is applied through an orifice in said tubular frame, whereby a partial vacuum develops in the chamber causing said sheet to closely conform to the body of the animal while exerting an essentially constant pressure thereon, thereby restraining the animal.

* * * * *